US012035880B2

(12) United States Patent
Scheib et al.

(10) Patent No.: US 12,035,880 B2
(45) Date of Patent: Jul. 16, 2024

(54) SURGICAL VISUALIZATION SYSTEM WITH FIELD OF VIEW WINDOWING

(71) Applicant: Cilag GmbH International, Zug (CH)

(72) Inventors: Charles J. Scheib, Loveland, OH (US); Paul G. Ritchie, Loveland, OH (US); Sarah A. Moore, Los Gatos, CA (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/528,759

(22) Filed: Nov. 17, 2021

(65) Prior Publication Data

US 2023/0148835 A1    May 18, 2023

(51) Int. Cl.
*A61B 1/00* (2006.01)
*A61B 1/045* (2006.01)
*A61B 1/05* (2006.01)
*A61B 1/06* (2006.01)

(52) U.S. Cl.
CPC ...... *A61B 1/0005* (2013.01); *A61B 1/000095* (2022.02); *A61B 1/00096* (2013.01); *A61B 1/045* (2013.01); *A61B 1/051* (2013.01); *A61B 1/0638* (2013.01); *A61B 1/0676* (2013.01); *A61B 1/00087* (2013.01)

(58) Field of Classification Search
CPC .......... A61B 1/00009; A61B 1/000095; A61B 1/00045; A61B 1/0005; A61B 1/00087; A61B 1/00183; A61B 1/045; A61B 1/51; A61B 1/000096; A61B 1/00006; A61B 1/00181
See application file for complete search history.

(56) References Cited

U.S. PATENT DOCUMENTS

| | | | |
|---|---|---|---|
| 6,387,043 B1* | 5/2002 | Yoon | A61B 1/05 600/129 |
| 9,274,047 B2 | 3/2016 | Velten et al. | |
| 2005/0010082 A1* | 1/2005 | Nishimura | A61B 1/00009 600/145 |
| 2010/0076263 A1* | 3/2010 | Tanaka | A61B 1/00042 600/109 |
| 2010/0317965 A1* | 12/2010 | Itkowitz | A61B 1/00194 382/128 |
| 2016/0174814 A1* | 6/2016 | Igov | A61B 1/00101 600/106 |
| 2017/0055819 A1 | 3/2017 | Hansen et al. | |

(Continued)

FOREIGN PATENT DOCUMENTS

JP    2012130505 A  *  7/2012

OTHER PUBLICATIONS

International Search Report and Written Opinion dated Feb. 1, 2023, for International Application No. PCT/IB2022/060675, 16 pages.

*Primary Examiner* — Aaron B Fairchild
(74) *Attorney, Agent, or Firm* — Frost Brown Todd LLP

(57) ABSTRACT

A surgical visualization system comprises: (a) a set of one or more imaging devices, wherein the set of one or more imaging devices is adapted to capture a view of an interior of a cavity of a patient; (b) a display; and (c) a processor in operative communication with the set of one or more imaging devices and the display, wherein the processor is configured to present an interface on the display, the interface comprising a second field of view of the interior of the cavity of the patient, wherein the second field of view is comprised by the first field of view.

17 Claims, 11 Drawing Sheets

(56) References Cited

U.S. PATENT DOCUMENTS

| | | |
|---|---|---|
| 2017/0251900 A1 | 9/2017 | Hansen et al. |
| 2018/0296280 A1* | 10/2018 | Kurihara ................ A61B 34/74 |
| 2018/0297206 A1 | 10/2018 | Larkin et al. |
| 2019/0076202 A1* | 3/2019 | Weir .................... A61B 90/361 |
| 2019/0290371 A1 | 9/2019 | Calef et al. |
| 2020/0015668 A1 | 1/2020 | Scheib |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015907 A1 | 1/2020 | Scheib |
| 2020/0015923 A1 | 1/2020 | Scheib et al. |
| 2020/0015924 A1 | 1/2020 | Scheib et al. |
| 2020/0015925 A1* | 1/2020 | Scheib ................ A61B 1/0638 |
| 2021/0015343 A1* | 1/2021 | Uyama ............... A61B 1/00048 |
| 2021/0343088 A1* | 11/2021 | Payyavula ............. A61B 34/20 |
| 2022/0192777 A1* | 6/2022 | Kuroda .................. A61B 90/37 |
| 2023/0156174 A1 | 5/2023 | Kristensen et al. |

* cited by examiner

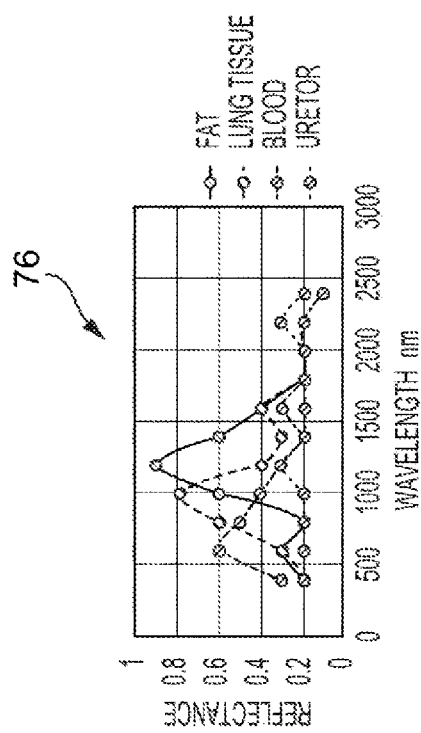
FIG. 4
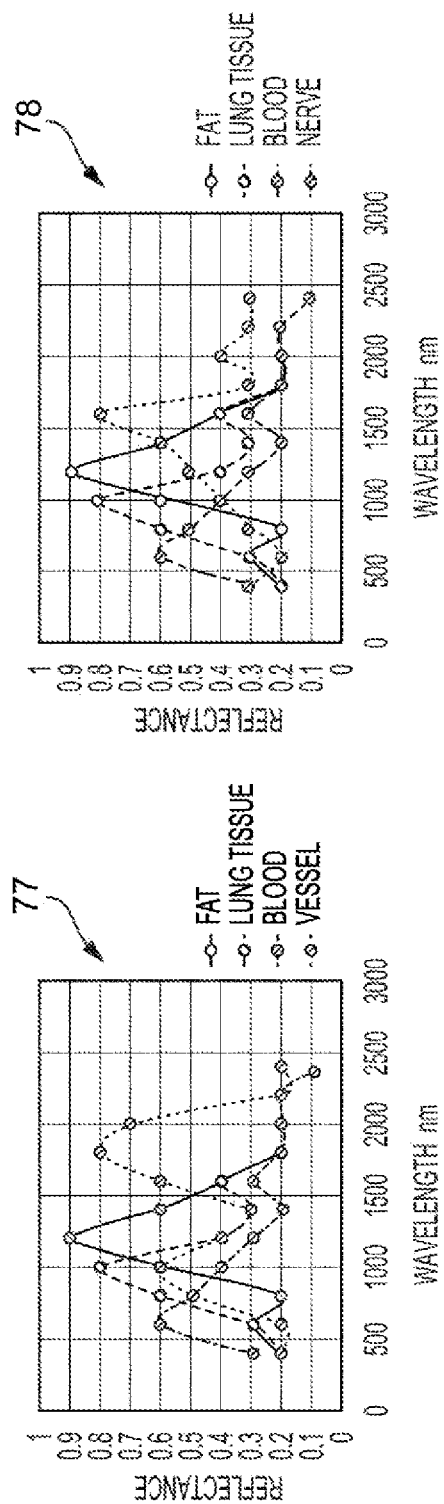
FIG. 5
FIG. 6

SURGICAL VISUALIZATION SYSTEM WITH FIELD OF VIEW WINDOWING

BACKGROUND

Surgical systems may incorporate an imaging system, which may allow the clinician(s) to view the surgical site and/or one or more portions thereof on one or more displays such as a monitor. The display(s) may be local and/or remote to a surgical theater. An imaging system may include a scope with a camera that views the surgical site and transmits the view to a display that is viewable by the clinician. Scopes include, but are not limited to, laparoscopes, robotic laparoscopes, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems may be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

Examples of surgical imaging systems are disclosed in U.S. Pat. Pub. No. 2020/0015925, entitled "Combination Emitter and Camera Assembly," published Jan. 16, 2020, issued as U.S. Pat. No. 11,754,712 on Sep. 12, 2023; U.S. Pat. Pub. No. 2020/0015923, entitled "Surgical Visualization Platform," published Jan. 16, 2020, issued as U.S. Pat. No. 11,000,270 on May 11, 2021; U.S. Pat. Pub. No. 2020/0015900, entitled "Controlling an Emitter Assembly Pulse Sequence," published Jan. 16, 2020; U.S. Pat. Pub. No. 2020/0015899, entitled "Surgical Visualization with Proximity Tracking Features," published Jan. 16, 2020; U.S. Pat. Pub. No. 2020/0015924, entitled "Robotic Light Projection Tools," published Jan. 16, 2020; and U.S. Pat. Pub. No. 2020/0015898, entitled "Surgical Visualization Feedback System," published Jan. 16, 2020, issued as U.S. Pat. No. 11,571,205 on Feb. 7, 2023. The disclosure of each of the above-cited U.S. patents and patent applications is incorporated by reference herein.

While various kinds of surgical instruments and systems have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4 depicts exemplary hyperspectral identifying signatures to differentiate anatomy from obscurants, and more particularly depicts a graphical representation of a ureter signature versus obscurants;

FIG. 5 depicts exemplary hyperspectral identifying signatures to differentiate anatomy from obscurants, and more particularly depicts a graphical representation of an artery signature versus obscurants;

FIG. 6 depicts exemplary hyperspectral identifying signatures to differentiate anatomy from obscurants, and more particularly depicts a graphical representation of a nerve signature versus obscurants;

Figure 1:
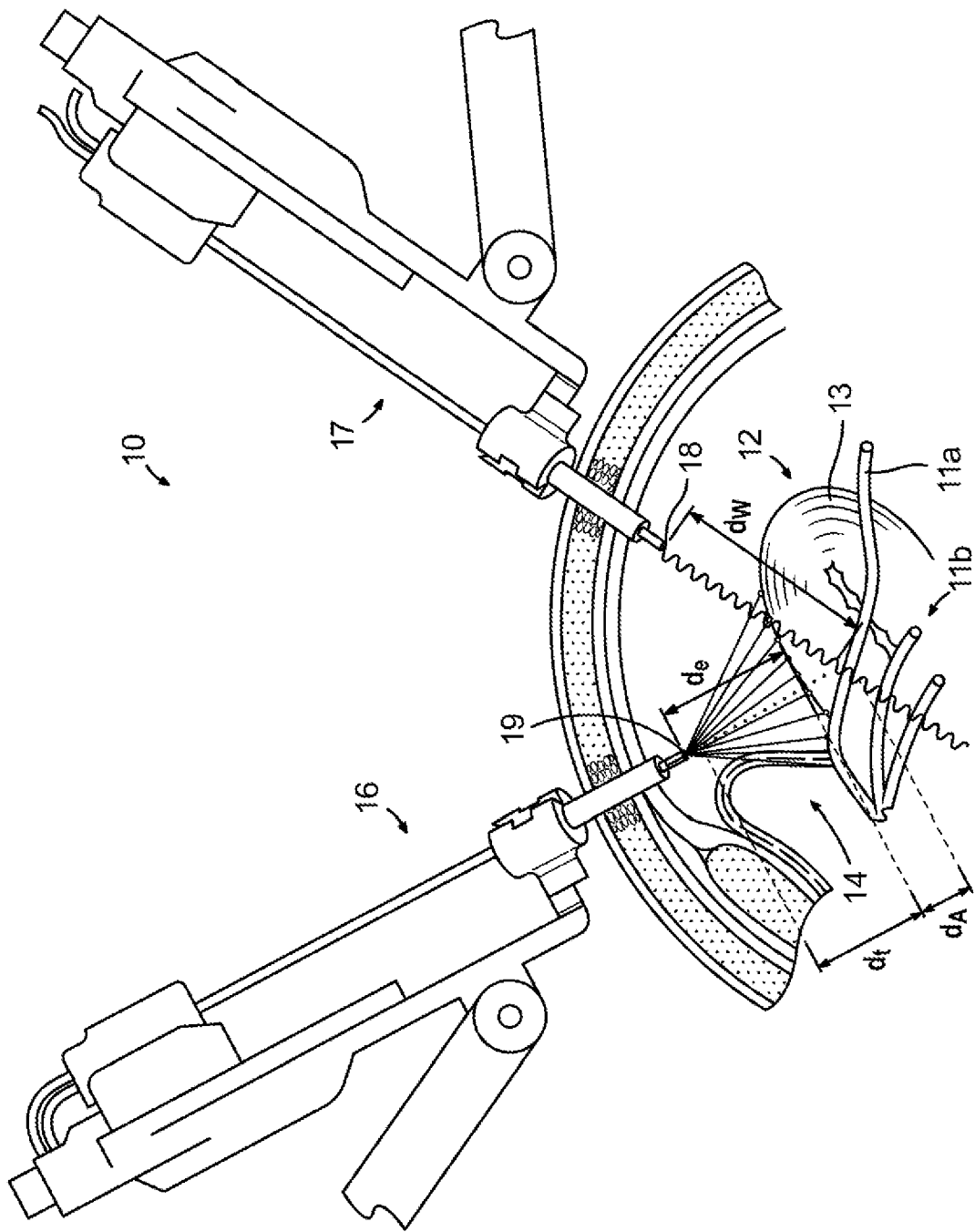
FIG. 1 depicts a schematic view of an exemplary surgical visualization system including an imaging device and a surgical device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

Similarly, the phrase "based on" should be understood as referring to a relationship in which one thing is determined at least in part by what it is specified as being "based on." This includes, but is not limited to, relationships where one thing is exclusively determined by another, which relationships may be referred to using the phrase "exclusively based on."

I. EXEMPLARY SURGICAL VISUALIZATION SYSTEM

FIG. 1 depicts a schematic view of a surgical visualization system (10) according to at least one aspect of the present disclosure. The surgical visualization system (10) may create a visual representation of a critical structure (11a, 11b) within an anatomical field. The surgical visualization system (10) may be used for clinical analysis and/or medical intervention, for example. In certain instances, the surgical visualization system (10) may be used intraoperatively to provide real-time, or near real-time, information to the clinician regarding proximity data, dimensions, and/or distances during a surgical procedure. The surgical visualization system (10) is configured for intraoperative identification of critical structure(s) and/or to facilitate the avoidance of critical structure(s) (11a, 11b) by a surgical device. For example, by identifying critical structures (11a, 11b), a clinician may avoid maneuvering a surgical device into a critical structure (11a, 11b) and/or a region in a predefined proximity of a critical structure (11a, 11b) during a surgical procedure. The clinician may avoid dissection of and/or near a vein, artery, nerve, and/or vessel, for example, identified as a critical structure (11a, 11b), for example. In various instances, critical structure(s) (11a, 11b) may be determined on a patient-by-patient and/or a procedure-by-procedure basis.

Critical structures (11a, 11b) may be any anatomical structures of interest. For example, a critical structure (11a, 11b) may be a ureter, an artery such as a superior mesenteric artery, a vein such as a portal vein, a nerve such as a phrenic nerve, and/or a sub-surface tumor or cyst, among other anatomical structures. In other instances, a critical structure (11a, 11b) may be any foreign structure in the anatomical field, such as a surgical device, surgical fastener, clip, tack, bougie, band, and/or plate, for example. In one aspect, a critical structure (11a, 11b) may be embedded in tissue. Stated differently, a critical structure (11a, 11b) may be positioned below a surface of the tissue. In such instances, the tissue conceals the critical structure (11a, 11b) from the clinician's view. A critical structure (11a, 11b) may also be obscured from the view of an imaging device by the tissue. The tissue may be fat, connective tissue, adhesions, and/or organs, for example. In other instances, a critical structure (11a, 11b) may be partially obscured from view. A surgical visualization system (10) is shown being utilized intraoperatively to identify and facilitate avoidance of certain critical structures, such as a ureter (11a) and vessels (11b) in an organ (12) (the uterus in this example), that are not visible on a surface (13) of the organ (12).

A. Overview of Exemplary Surgical Visualization System

With continuing reference to FIG. 1, the surgical visualization system (10) incorporates tissue identification and geometric surface mapping in combination with a distance sensor system (14). In combination, these features of the surgical visualization system (10) may determine a position of a critical structure (11a, 11b) within the anatomical field and/or the proximity of a surgical device (16) to the surface (13) of the visible tissue and/or to a critical structure (11a, 11b). The surgical device (16) may include an end effector having opposing jaws (not shown) and/or other structures extending from the distal end of the shaft of the surgical device (16). The surgical device (16) may be any suitable surgical device such as, for example, a dissector, a stapler, a grasper, a clip applier, a monopolar RF electrosurgical instrument, a bipolar RF electrosurgical instrument, and/or an ultrasonic instrument. As described herein, a surgical visualization system (10) may be configured to achieve identification of one or more critical structures (11a, 11b) and/or the proximity of a surgical device (16) to critical structure(s) (11a, 11b).

The depicted surgical visualization system (10) includes an imaging system that includes an imaging device (17), such as a camera or a scope, for example, that is configured to provide real-time views of the surgical site. In various instances, an imaging device (17) includes a spectral camera (e.g., a hyperspectral camera, multispectral camera, a fluorescence detecting camera, or selective spectral camera), which is configured to detect reflected or emitted spectral waveforms and generate a spectral cube of images based on the molecular response to the different wavelengths. Views from the imaging device (17) may be provided to a clinician; and, in various aspects of the present disclosure, may be augmented with additional information based on the tissue identification, landscape mapping, and input from a distance sensor system (14). In such instances, a surgical visualization system (10) includes a plurality of subsystems—an imaging subsystem, a surface mapping subsystem, a tissue identification subsystem, and/or a distance determining subsystem. These subsystems may cooperate to intraoperatively provide advanced data synthesis and integrated information to the clinician(s).

The imaging device (17) of the present example includes an emitter (18), which is configured to emit spectral light in a plurality of wavelengths to obtain a spectral image of hidden structures, for example. The imaging device (17) may also include a three-dimensional camera and associated electronic processing circuits in various instances. In one aspect, the emitter (18) is an optical waveform emitter that is configured to emit electromagnetic radiation (e.g., near-infrared radiation (NIR) photons) that may penetrate the surface (13) of a tissue (12) and reach critical structure(s) (11a, 11b). The imaging device (17) and optical waveform emitter (18) thereon may be positionable by a robotic arm or a surgeon manually operating the imaging device. A corresponding waveform sensor (e.g., an image sensor, spectrometer, or vibrational sensor, etc.) on the imaging device (17) may be configured to detect the effect of the electromagnetic radiation received by the waveform sensor.

The wavelengths of the electromagnetic radiation emitted by the optical waveform emitter (18) may be configured to enable the identification of the type of anatomical and/or physical structure, such as critical structure(s) (11a, 11b). The identification of critical structure(s) (11a, 11b) may be accomplished through spectral analysis, photo-acoustics, fluorescence detection, and/or ultrasound, for example. In one aspect, the wavelengths of the electromagnetic radiation may be variable. The waveform sensor and optical waveform emitter (18) may be inclusive of a multispectral imaging system and/or a selective spectral imaging system, for example. In other instances, the waveform sensor and optical waveform emitter (18) may be inclusive of a photoacoustic imaging system, for example. In other instances, an optical waveform emitter (18) may be positioned on a separate surgical device from the imaging device (17). By way of example only, the imaging device (17) may provide hyperspectral imaging in accordance with at least some of the teachings of U.S. Pat. No. 9,274,047, entitled "System and Method for Gross Anatomic Pathology Using Hyperspectral Imaging," issued Mar. 1, 2016, the disclosure of which is incorporated by reference herein in its entirety.

The depicted surgical visualization system (10) also includes an emitter (19), which is configured to emit a pattern of light, such as stripes, grid lines, and/or dots, to enable the determination of the topography or landscape of a surface (13). For example, projected light arrays may be used for three-dimensional scanning and registration on a surface (13). The projected light arrays may be emitted from an emitter (19) located on a surgical device (16) and/or an imaging device (17), for example. In one aspect, the projected light array is employed to determine the shape defined by the surface (13) of the tissue (12) and/or the motion of the surface (13) intraoperatively. An imaging device (17) is configured to detect the projected light arrays reflected from the surface (13) to determine the topography of the surface (13) and various distances with respect to the surface (13). By way of further example only, a visualization system (10) may utilize patterned light in accordance with at least some of the teachings of U.S. Pat. Pub. No. 2017/0055819, entitled "Set Comprising a Surgical Instrument," published Mar. 2, 2017, issued as U.S. Pat. No. 11,033,182 on Jun. 15, 2021, the disclosure of which is incorporated by reference herein in its entirety; and/or U.S. Pat. Pub. No. 2017/0251900, entitled "Depiction System," published Sep. 7, 2017, issued as U.S. Pat. No. 11,039,734 on Jun. 22, 2021, the disclosure of which is incorporated by reference herein in its entirety.

The depicted surgical visualization system (10) also includes a distance sensor system (14) configured to determine one or more distances at the surgical site. In one aspect, the distance sensor system (14) may include a time-of-flight distance sensor system that includes an emitter, such as the structured light emitter (19); and a receiver (not shown), which may be positioned on the surgical device (16). In other instances, the time-of-flight emitter may be separate from the structured light emitter. In one general aspect, the emitter portion of the time-of-flight distance sensor system (14) may include a laser source and the receiver portion of the time-of-flight distance sensor system (14) may include a matching sensor. A time-of-flight distance sensor system (14) may detect the "time of flight," or how long the laser light emitted by the structured light emitter (19) has taken to bounce back to the sensor portion of the receiver. Use of a very narrow light source in a structured light emitter (19) may enable a distance sensor system (14) to determine the distance to the surface (13) of the tissue (12) directly in front of the distance sensor system (14).

Referring still to FIG. 1, a distance sensor system (14) may be employed to determine an emitter-to-tissue distance ($d_e$) from a structured light emitter (19) to the surface (13) of the tissue (12). A device-to-tissue distance ($d_t$) from the distal end of the surgical device (16) to the surface (13) of the tissue (12) may be obtainable from the known position of the emitter (19) on the shaft of the surgical device (16) relative to the distal end of the surgical device (16). In other words, when the distance between the emitter (19) and the distal end of the surgical device (16) is known, the device-to-tissue distance ($d_t$) may be determined from the emitter-to-tissue distance ($d_e$). In certain instances, the shaft of a surgical device (16) may include one or more articulation joints; and may be articulatable with respect to the emitter (19) and the jaws. The articulation configuration may include a multi-joint vertebrae-like structure, for example. In certain instances, a three-dimensional camera may be utilized to triangulate one or more distances to the surface (13).

As described above, a surgical visualization system (10) may be configured to determine the emitter-to-tissue distance ($d_e$) from an emitter (19) on a surgical device (16) to the surface (13) of a uterus (12) via structured light. The surgical visualization system (10) is configured to extrapolate a device-to-tissue distance ($d_t$) from the surgical device (16) to the surface (13) of the uterus (12) based on emitter-to-tissue distance ($d_e$). The surgical visualization system (10) is also configured to determine a tissue-to-ureter distance ($d_A$) from a ureter (11a) to the surface (13) and a camera-to-ureter distance ($d_w$), from the imaging device (17) to the ureter (11a). Surgical visualization system (10) may determine the camera-to-ureter distance ($d_w$), with spectral imaging and time-of-flight sensors, for example. In various instances, a surgical visualization system (10) may determine (e.g., triangulate) a tissue-to-ureter distance ($d_A$) (or depth) based on other distances and/or the surface mapping logic described herein.

B. First Exemplary Control System

Figure 2:
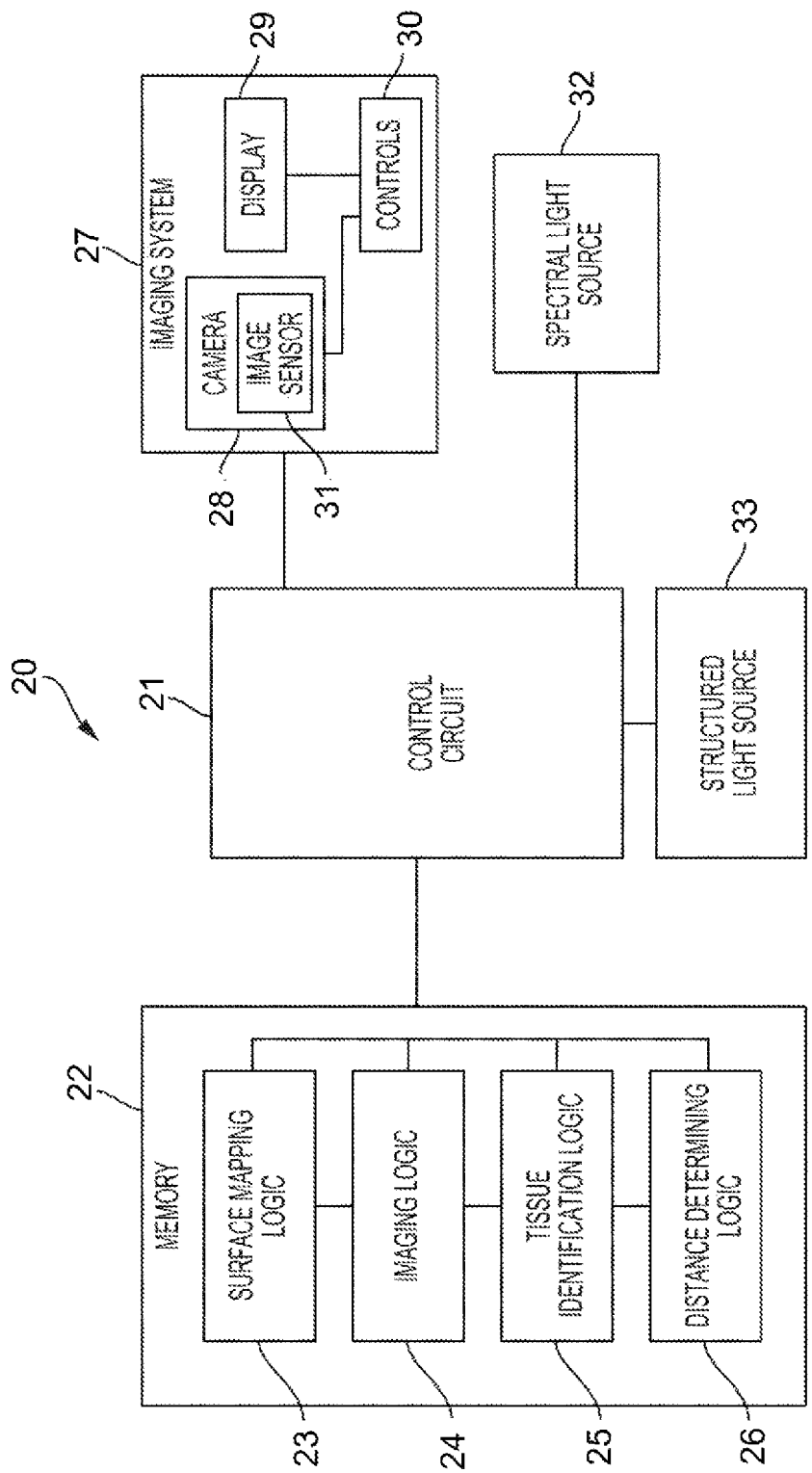
FIG. 2 depicts a schematic diagram of an exemplary control system that may be used with the surgical visualization system of FIG. 1.

FIG. 2 is a schematic diagram of a control system (20), which may be utilized with a surgical visualization system (10). The depicted control system (20) includes a control circuit (21) in signal communication with a memory (22). The memory (22) stores instructions executable by the control circuit (21) to determine and/or recognize critical structures (e.g., critical structures (11a, 11b) depicted in FIG. 1), determine and/or compute one or more distances and/or three-dimensional digital representations, and to communicate certain information to one or more clinicians. For example, a memory (22) stores surface mapping logic (23), imaging logic (24), tissue identification logic (25), or distance determining logic (26) or any combinations of logic (23, 24, 25, 26). The control system (20) also includes an imaging system (27) having one or more cameras (28) (like the imaging device (17) depicted in FIG. 1), one or more displays (29), one or more controls (30) or any combinations of these elements. The one or more cameras (28) may include one or more image sensors (31) to receive signals from various light sources emitting light at various visible and invisible spectra (e.g., visible light, spectral imagers, three-dimensional lens, among others). The display (29) may include one or more screens or monitors for depicting real, virtual, and/or virtually-augmented images and/or information to one or more clinicians.

In various aspects, a main component of a camera (28) includes an image sensor (31). An image sensor (31) may include a Charge-Coupled Device (CCD) sensor, a Complementary Metal Oxide Semiconductor (CMOS) sensor, a short-wave infrared (SWIR) sensor, a hybrid CCD/CMOS architecture (sCMOS) sensor, and/or any other suitable kind(s) of technology. An image sensor (31) may also include any suitable number of chips.

The depicted control system (20) also includes a spectral light source (32) and a structured light source (33). In certain instances, a single source may be pulsed to emit wavelengths of light in the spectral light source (32) range and wavelengths of light in the structured light source (33) range. Alternatively, a single light source may be pulsed to provide light in the invisible spectrum (e.g., infrared spectral light) and wavelengths of light on the visible spectrum. A spectral light source (32) may include a hyperspectral light source, a multispectral light source, a fluorescence excitation light source, and/or a selective spectral light source, for example. In various instances, tissue identification logic (25) may identify critical structure(s) via data from a spectral light source (32) received by the image sensor (31) portion of a camera (28). Surface mapping logic (23) may determine the surface contours of the visible tissue based on reflected structured light. With time-of-flight measurements, distance determining logic (26) may determine one or more distance (s) to the visible tissue and/or critical structure(s) (11a, 11b). One or more outputs from surface mapping logic (23), tissue identification logic (25), and distance determining logic (26), may be provided to imaging logic (24), and combined, blended, and/or overlaid to be conveyed to a clinician via the display (29) of the imaging system (27).

C. Second Exemplary Control System

Figure 3:
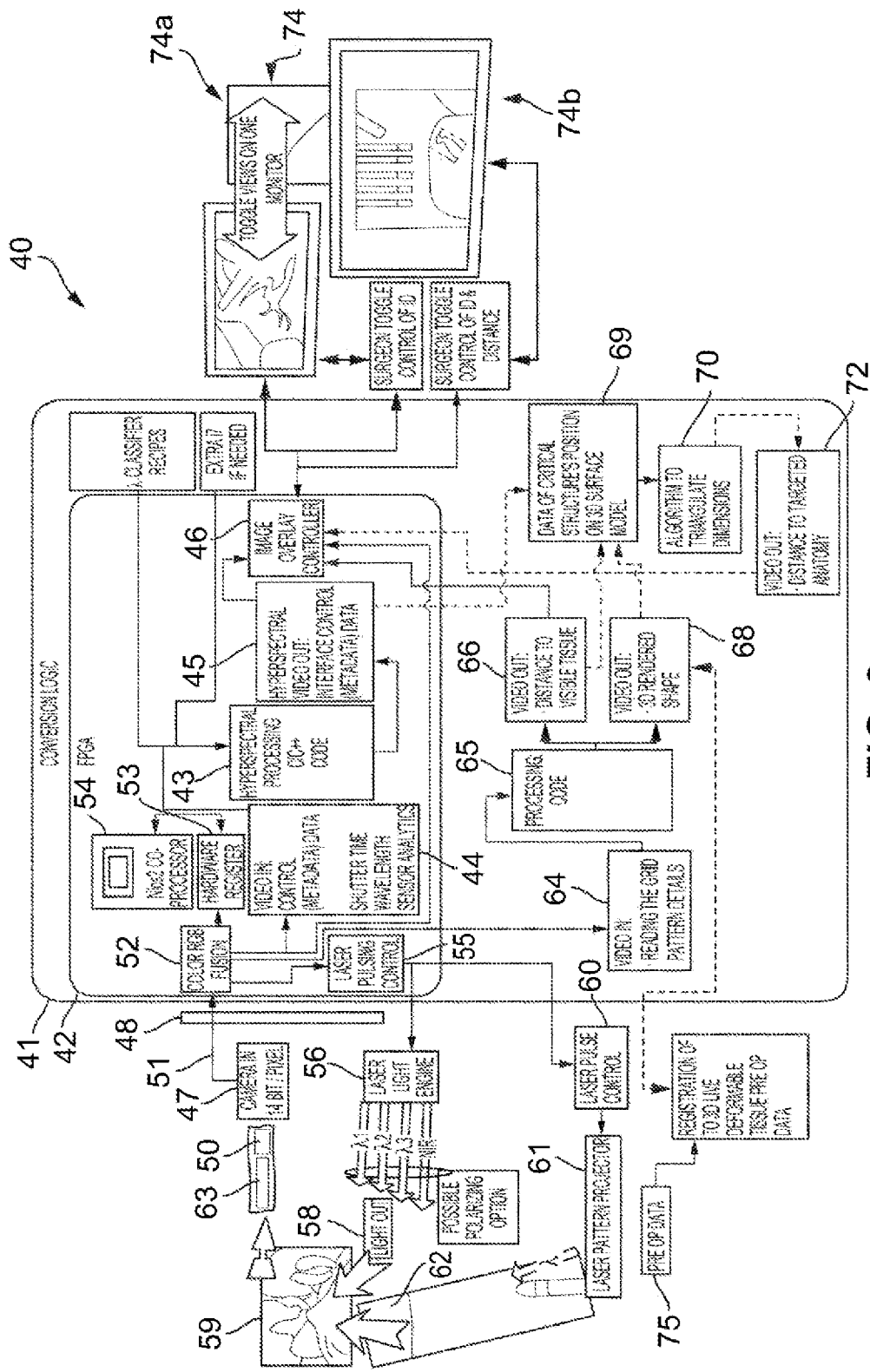
FIG. 3 depicts a schematic diagram of another exemplary control system that may be used with the surgical visualization system of FIG. 1.

FIG. 3 depicts a schematic of another control system (40) for a surgical visualization system, such as the surgical visualization system (10) depicted in FIG. 1, for example. This control system (40) is a conversion system that integrates spectral signature tissue identification and structured light tissue positioning to identify critical structures, especially when those structures are obscured by other tissue, such as fat, connective tissue, blood, and/or other organs, for example. Such technology could also be useful for detecting tissue variability, such as differentiating tumors and/or non-healthy tissue from healthy tissue within an organ.

The control system (40) depicted in FIG. 3 is configured for implementing a hyperspectral or fluorescence imaging and visualization system in which a molecular response is utilized to detect and identify anatomy in a surgical field of view. This control system (40) includes a conversion logic circuit (41) to convert tissue data to surgeon usable information. For example, the variable reflectance based on wavelengths with respect to obscuring material may be utilized to identify a critical structure in the anatomy. Moreover, this control system (40) combines the identified spectral signature and the structured light data in an image. For example, this control system (40) may be employed to create a three-dimensional data set for surgical use in a system with augmentation image overlays. Techniques may be employed both intraoperatively and preoperatively using additional visual information. In various instances, this control system (40) is configured to provide warnings to a clinician when in the proximity of one or more critical structures. Various algorithms may be employed to guide robotic automation and semi-automated approaches based on the surgical procedure and proximity to the critical structure(s).

The control system (40) depicted in FIG. 3 is configured to detect the critical structure(s) and provide an image overlay of the critical structure and measure the distance to the surface of the visible tissue and the distance to the embedded/buried critical structure(s). In other instances, this control system (40) may measure the distance to the surface of the visible tissue or detect the critical structure(s) and provide an image overlay of the critical structure.

The control system (40) depicted in FIG. 3 includes a spectral control circuit (42). The spectral control circuit (42) includes a processor (43) to receive video input signals from a video input processor (44). The processor (43) is configured to process the video input signal from the video input processor (44) and provide a video output signal to a video output processor (45), which includes a hyperspectral video-out of interface control (metadata) data, for example. The video output processor (45) provides the video output signal to an image overlay controller (46).

The video input processor (44) is coupled to a camera (47) at the patient side via a patient isolation circuit (48). As previously discussed, the camera (47) includes a solid state image sensor (50). The camera (47) receives intraoperative images through optics (63) and the image sensor (50). An isolated camera output signal (51) is provided to a color RGB fusion circuit (52), which employs a hardware register (53) and a Nios2 co-processor (54) to process the camera output signal (51). A color RGB fusion output signal is provided to the video input processor (44) and a laser pulsing control circuit (55).

The laser pulsing control circuit (55) controls a light engine (56). In some versions, light engine (56) includes any one or more of lasers, LEDs, incandescent sources, and/or interface electronics configured to illuminate the patient's body habitus with a chosen light source for imaging by a camera and/or analysis by a processor. The light engine (56) outputs light in a plurality of wavelengths ($\lambda 1, \lambda 2, \lambda 3 \ldots \lambda n$) including near infrared (NIR) and broadband white light. The light output (58) from the light engine (56) illuminates targeted anatomy in an intraoperative surgical site (59). The laser pulsing control circuit (55) also controls a laser pulse controller (60) for a laser pattern projector (61) that projects a laser light pattern (62), such as a grid or pattern of lines and/or dots, at a predetermined wavelength ($\lambda 2$) on the operative tissue or organ at the surgical site (59). the camera (47) receives the patterned light as well as the reflected or emitted light output through camera optics (63). The image sensor (50) converts the received light into a digital signal.

The color RGB fusion circuit (52) also outputs signals to the image overlay controller (46) and a video input module (64) for reading the laser light pattern (62) projected onto the targeted anatomy at the surgical site (59) by the laser pattern projector (61). A processing module (65) processes the laser light pattern (62) and outputs a first video output signal (66) representative of the distance to the visible tissue at the surgical site (59). The data is provided to the image overlay controller (46). The processing module (65) also outputs a second video signal (68) representative of a three-dimensional rendered shape of the tissue or organ of the targeted anatomy at the surgical site.

The first and second video output signals (66, 68) include data representative of the position of the critical structure on a three-dimensional surface model, which is provided to an integration module (69). In combination with data from the video output processor (45) of the spectral control circuit (42), the integration module (69) may determine distance ($d_A$) (FIG. 1) to a buried critical structure (e.g., via triangularization algorithms (70)), and that distance ($d_A$) may be provided to the image overlay controller (46) via a video out processor (72). The foregoing conversion logic may encompass a conversion logic circuit (41), intermediate video monitors (74), and a camera (56)/laser pattern projector (61) positioned at surgical site (59).

Preoperative data (75) from a CT or MRI scan may be employed to register or align certain three-dimensional deformable tissue in various instances. Such preoperative data (75) may be provided to an integration module (69) and ultimately to the image overlay controller (46) so that such information may be overlaid with the views from the camera (47) and provided to video monitors (74). Registration of preoperative data is further described herein and in U.S. Pat.

Pub. No. 2020/0015907, entitled "Integration of Imaging Data," published Jan. 16, 2020, for example, which is incorporated by reference herein in its entirety.

Video monitors (74) may output the integrated/augmented views from the image overlay controller (46). On a first monitor (74a), the clinician may toggle between (A) a view in which a three-dimensional rendering of the visible tissue is depicted and (B) an augmented view in which one or more hidden critical structures are depicted over the three-dimensional rendering of the visible tissue. On a second monitor (74b), the clinician may toggle on distance measurements to one or more hidden critical structures and/or the surface of visible tissue, for example.

D. Exemplary Hyperspectral Identifying Signatures

FIG. 4 depicts a graphical representation (76) of an illustrative ureter signature versus obscurants. The plots represent reflectance as a function of wavelength (nm) for wavelengths for fat, lung tissue, blood, and a ureter. FIG. 5 depicts a graphical representation (77) of an illustrative artery signature versus obscurants. The plots represent reflectance as a function of wavelength (nm) for fat, lung tissue, blood, and a vessel. FIG. 6 depicts a graphical representation (78) of an illustrative nerve signature versus obscurants. The plots represent reflectance as a function of wavelength (nm) for fat, lung tissue, blood, and a nerve.

In various instances, select wavelengths for spectral imaging may be identified and utilized based on the anticipated critical structures and/or obscurants at a surgical site (i.e., "selective spectral" imaging). By utilizing selective spectral imaging, the amount of time required to obtain the spectral image may be minimized such that the information may be obtained in real-time, or near real-time, and utilized intraoperatively. In various instances, the wavelengths may be selected by a clinician or by a control circuit based on input by the clinician. In certain instances, the wavelengths may be selected based on machine learning and/or big data accessible to the control circuit via a cloud, for example.

E. Exemplary Singular EMR Source Emitter Assembly

Figure 7A:
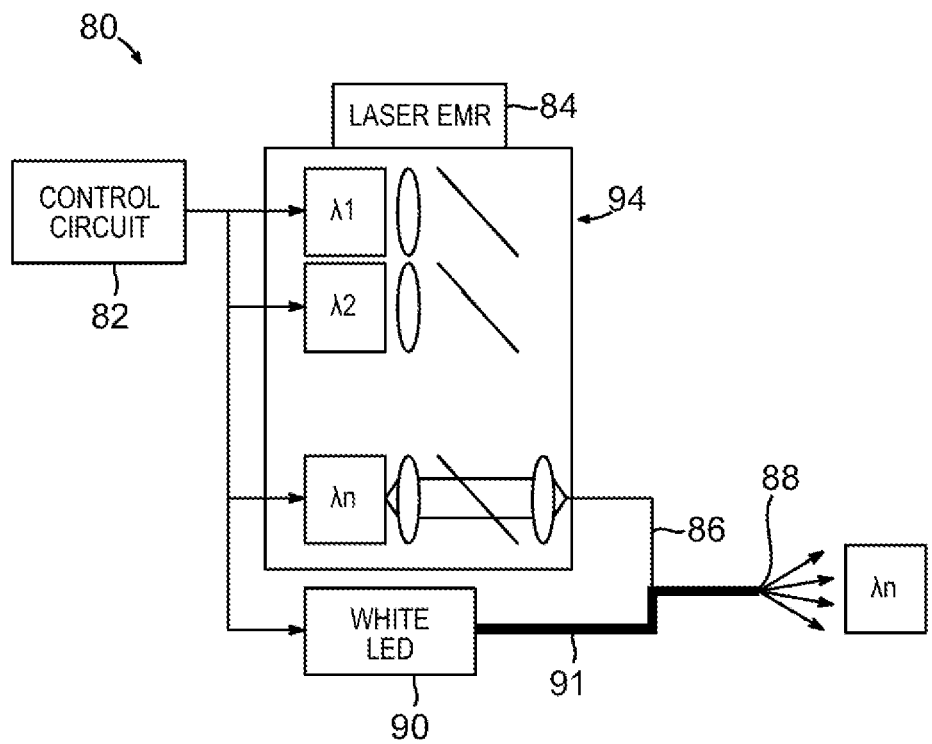
FIG. 7A depicts a schematic view of an exemplary emitter assembly that may be incorporated into the surgical visualization system of FIG. 1, the emitter assembly including a single electromagnetic radiation (EMR) source, showing the emitter assembly in a first state.
Figure 7B:
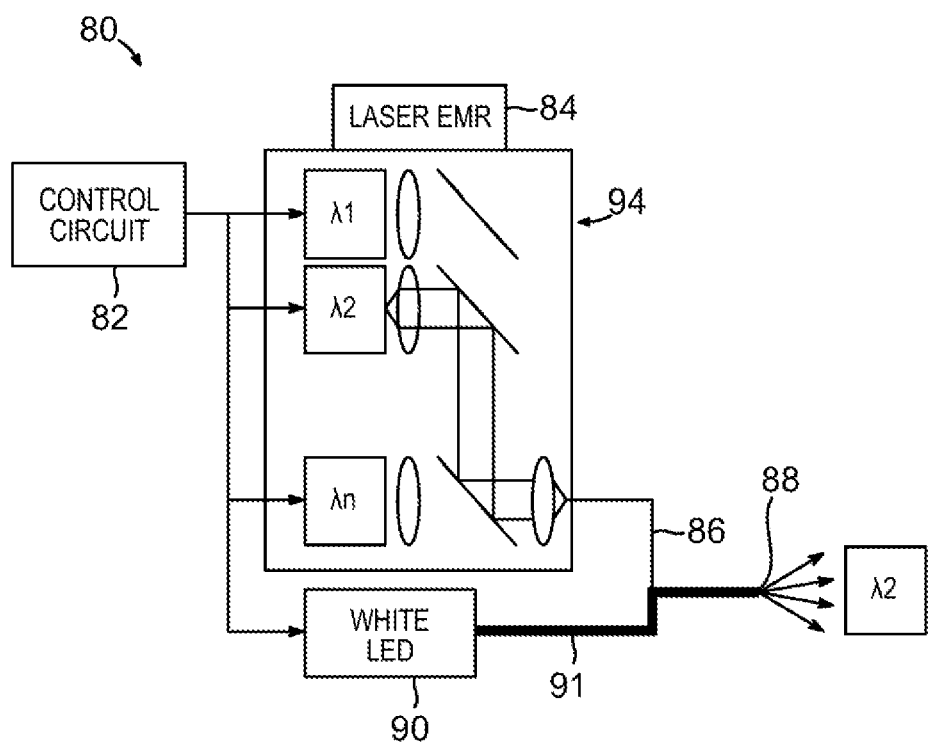
FIG. 7B depicts a schematic view of the emitter assembly of FIG. 7A, showing the emitter assembly in a second state.
Figure 7C:
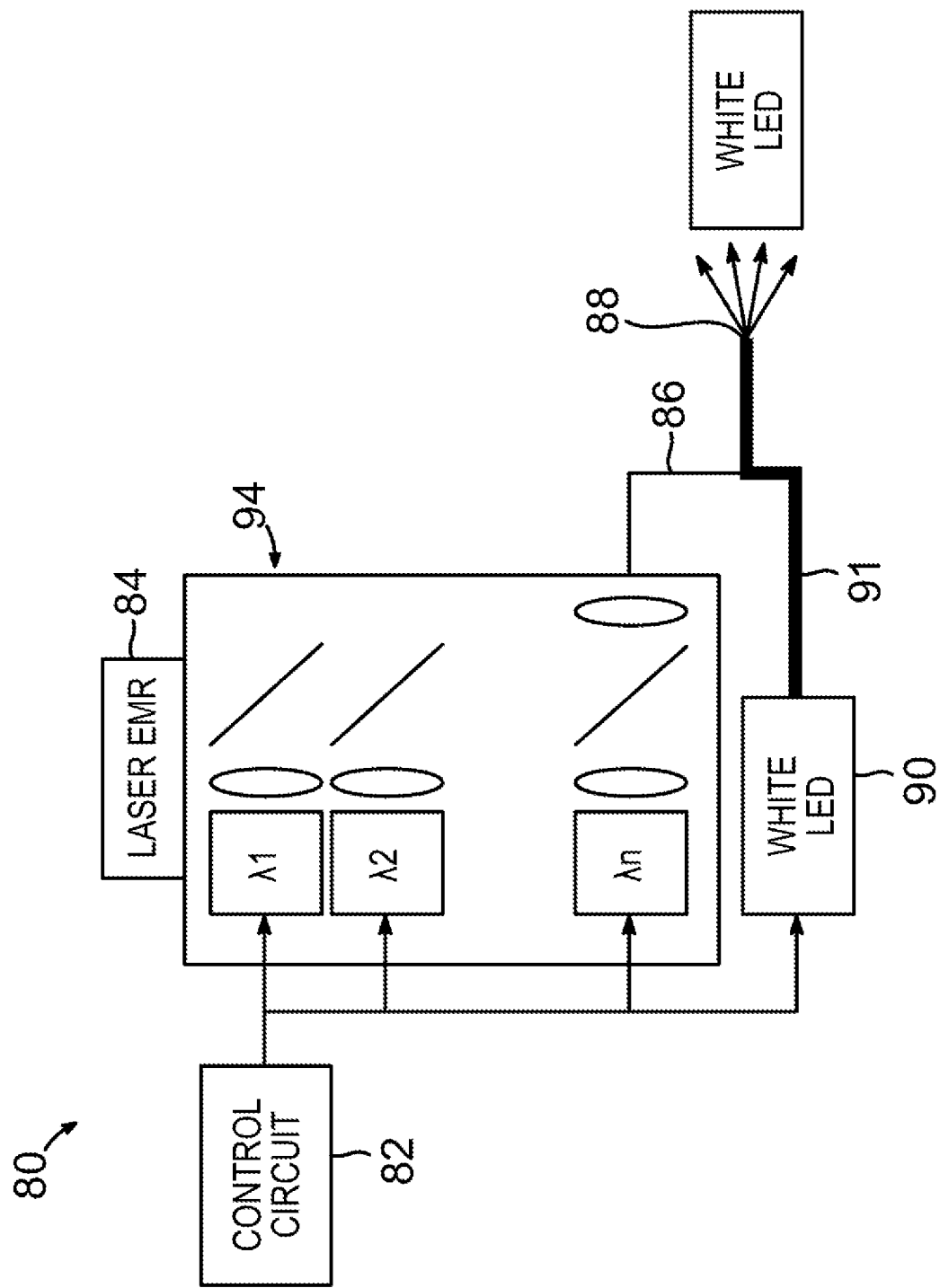
FIG. 7C depicts a schematic view of the emitter assembly of FIG. 7A, showing the emitter assembly in a third state.

Referring now to FIGS. 7A-7C, in one aspect, a visualization system (10) includes a receiver assembly (e.g., positioned on a surgical device (16)), which may include a camera (47) including an image sensor (50) (FIG. 3), and an emitter assembly (80) (e.g., positioned on imaging device (17)), which may include an emitter (18) (FIG. 1) and/or a light engine (56) (FIG. 3). Further, a visualization system (10) may include a control circuit (82), which may include the control circuit (21) depicted in FIG. 2 and/or the spectral control circuit (42) depicted in FIG. 3, coupled to each of emitter assembly (80) and the receiver assembly. An emitter assembly (80) may be configured to emit EMR at a variety of wavelengths (e.g., in the visible spectrum and/or in the IR spectrum) and/or as structured light (i.e., EMR projected in a particular known pattern). A control circuit (82) may include, for example, hardwired circuitry, programmable circuitry (e.g., a computer processor coupled to a memory or field programmable gate array), state machine circuitry, firmware storing instructions executed by programmable circuitry, and any combination thereof.

In one aspect, an emitter assembly (80) may be configured to emit visible light, IR, and/or structured light from a single EMR source (84). For example, FIGS. 7A-7C illustrate a diagram of an emitter assembly (80) in alternative states, in accordance with at least one aspect of the present disclosure. In this aspect, an emitter assembly (80) comprises a channel (86) connecting an EMR source (84) to an emitter (88) configured to emit visible light (e.g., RGB), IR, and/or structured light in response to being supplied EMR of particular wavelengths from the EMR source (84). The channel (86) may include, for example, a fiber optic cable. The EMR source (84) may include, for example, a light engine (56) (FIG. 3) including a plurality of light sources configured to selectively output light at respective wavelengths. In the example shown, the emitter assembly (80) also comprises a white LED (90) connected to the emitter (88) via another channel (91).

The depicted emitter assembly (80) further includes a wavelength selector assembly (94) configured to direct EMR emitted from the light sources of the EMR source (84) toward the first emitter (88). In the depicted aspect, the wavelength selector assembly (94) includes a plurality of deflectors and/or reflectors configured to transmit EMR from the light sources of the EMR source (84) to the emitter (88).

In one aspect, a control circuit (82) may be electrically coupled to each light source of the EMR source (84) such that it may control the light outputted therefrom via applying voltages or control signals thereto. The control circuit (82) may be configured to control the light sources of the EMR source (84) to direct EMR from the EMR source (84) to the emitter (88) in response to, for example, user input and/or detected parameters (e.g., parameters associated with the surgical instrument or the surgical site). In one aspect, the control circuit (82) is coupled to the EMR source (84) such that it may control the wavelength of the EMR generated by the EMR source (84). In various aspects, the control circuit (82) may control the light sources of the EMR source (84) either independently or in tandem with each other.

In some aspects, the control circuit (82) may adjust the wavelength of the EMR generated by the EMR source (84) according to which light sources of the EMR source (84) are activated. In other words, the control circuit (82) may control the EMR source (84) so that it produces EMR at a particular wavelength or within a particular wavelength range. For example, in FIG. 7A, the control circuit (82) has applied control signals to the nth light source of the EMR source (84) to cause it to emit EMR at an nth wavelength ($\lambda$n), and has applied control signals to the remaining light sources of the EMR source (84) to prevent them from emitting EMR at their respective wavelengths. Conversely, in FIG. 7B the control circuit (82) has applied control signals to the second light source of the EMR source (84) to cause it to emit EMR at a second wavelength ($\lambda$2), and has applied control signals to the remaining light sources of the EMR source (84) to prevent them from emitting EMR at their respective wavelengths. Furthermore, in FIG. 7C the control circuit (82) has applied control signals to the light sources of the EMR source (84) to prevent them from emitting EMR at their respective wavelengths, and has applied control signals to a white LED source to cause it to emit white light.

In addition to the foregoing, at least part of any one or more of the surgical visualization system (10) depicted in FIG. 1, the control system (20) depicted in FIG. 2, the control system (40) depicted in FIG. 3, and/or the emitter assembly (80) depicted in FIGS. 7A and 7B may be configured and operable in accordance with at least some of the teachings of U.S. Pat. Pub. No. 2020/0015925, entitled "Combination Emitter and Camera Assembly," published Jan. 16, 2020, issued as U.S. Pat. No. 11,754,712 on Sep. 12, 2023, which is incorporated by reference above. In one aspect, a surgical visualization system (10) may be incorporated into a robotic system in accordance with at least some of such teachings.

II. EXEMPLARY SURGICAL VISUALIZATION SYSTEM WITH WINDOWING

Figure 8:
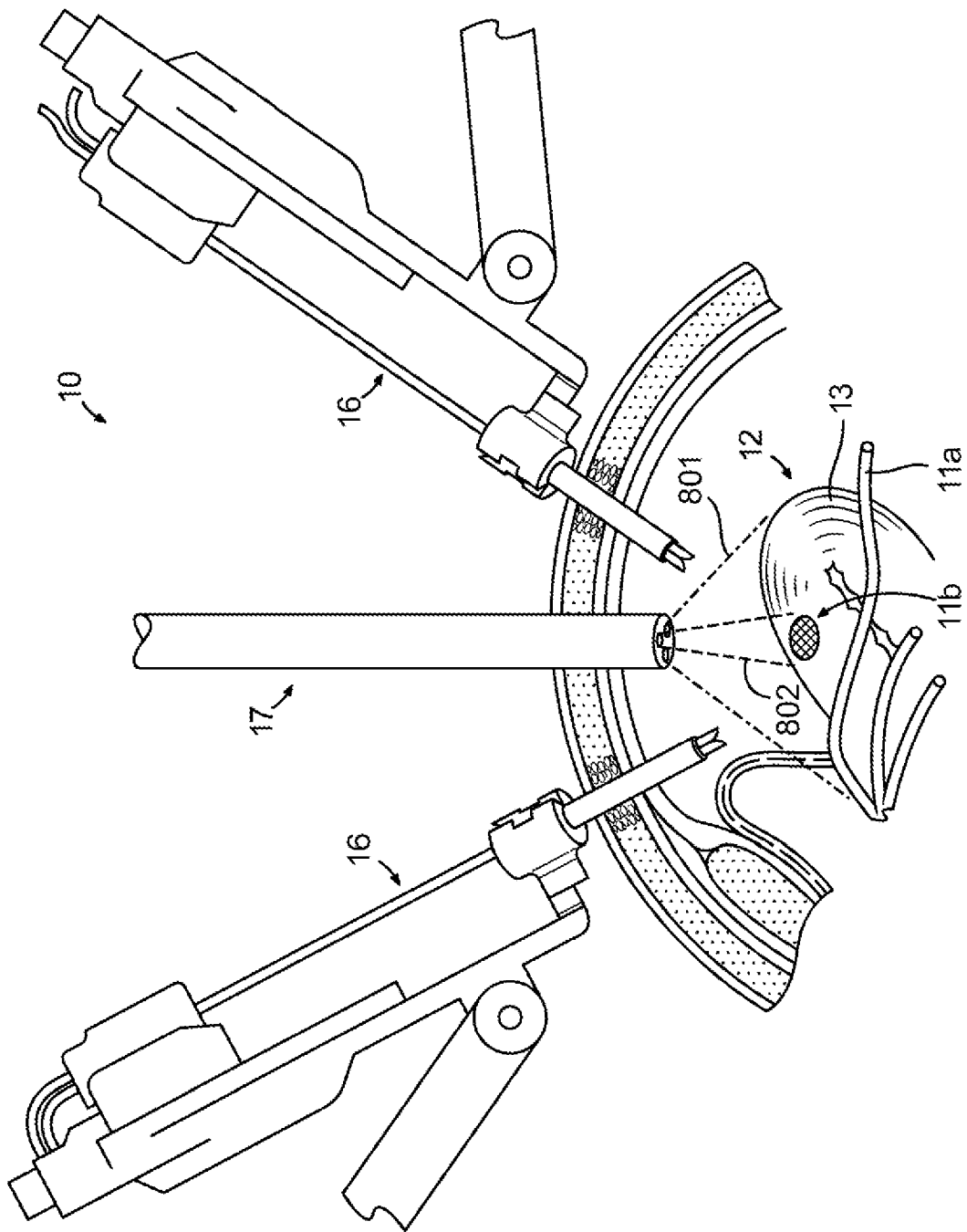
FIG. 8 depicts an exemplary surgical visualization system including an imaging device and a surgical device.

In some instances, it may be desirable to provide a surgical visualization system in which data provided to a surgeon (e.g., via display (29)) may be only a subset of data captured regarding the surgical field. This may, for example, allow for more effective visualization with visualization the surgeon needs most at the time he or she needs it. It may also reduce the computational burden on the surgical visualization system by reducing the processing associated with rendering an image for display. An example illustrating this type of approach is provided in FIG. 8. FIG. 8 depicts a scenario in which the imaging device (17) captures data regarding the anatomical field within a first field of view (801) of an anatomical field in which a surgeon would use one or more surgical devices (16) to perform a procedure. However, as shown in FIG. 8, in a case where the procedure focuses on a tumor or other critical structure (11b), all of the data regarding the entire first field of view may not be necessary, or may even be unhelpful and/or distracting to the surgeon. Instead, the surgeon may only desire to see data in a narrower second field of view (802). For example, if the first field of view (801) provides 270 degree visibility, only a smaller portion of that, such as a second field of view (802) of 42 degrees in the vertical direction and 72 degrees in the horizontal direction, may be useful to the surgeon.

Figure 9:
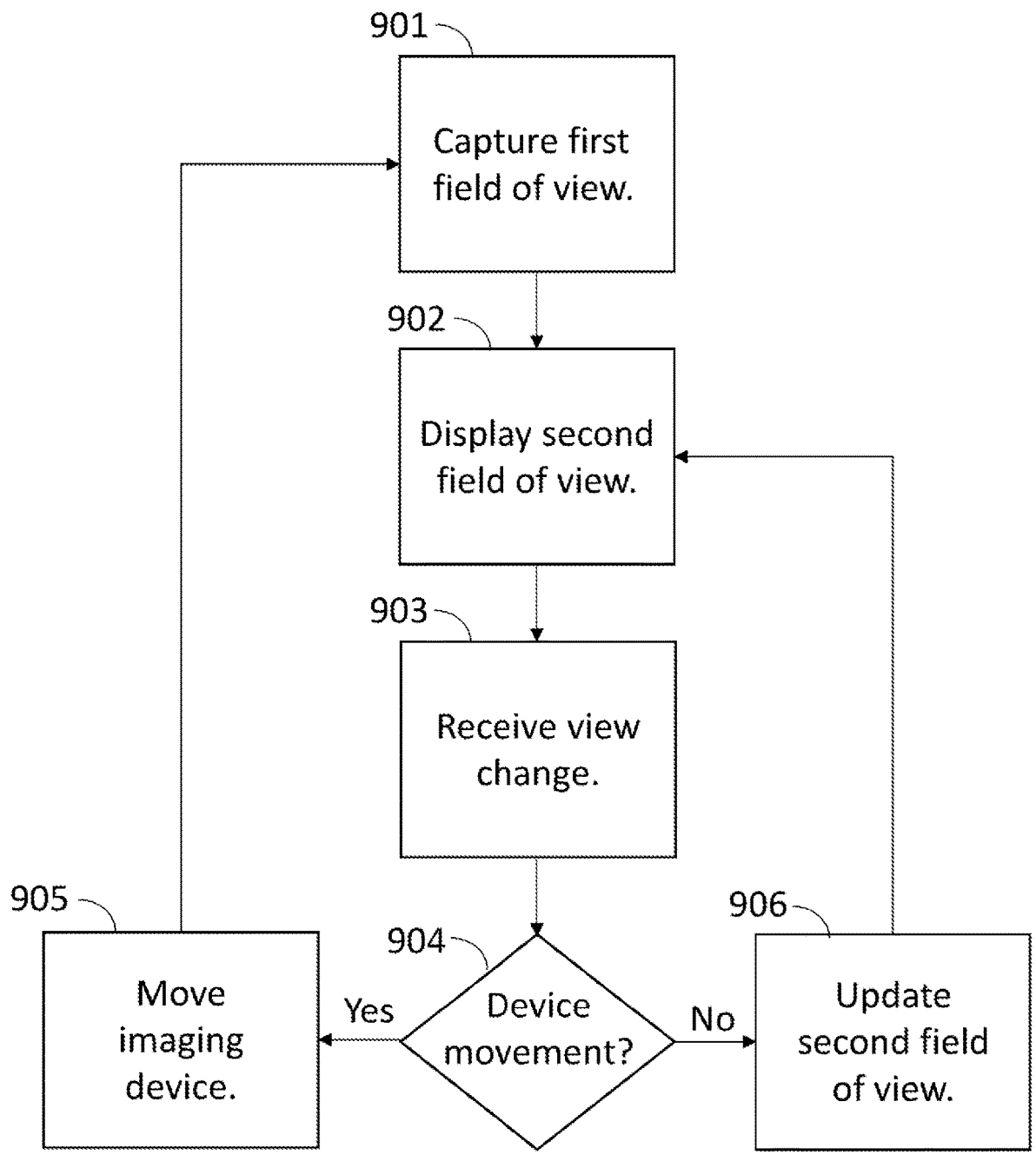
FIG. 9 depicts a method which may be used to allow a user to control a field of view which is displayed.
Figure 10:
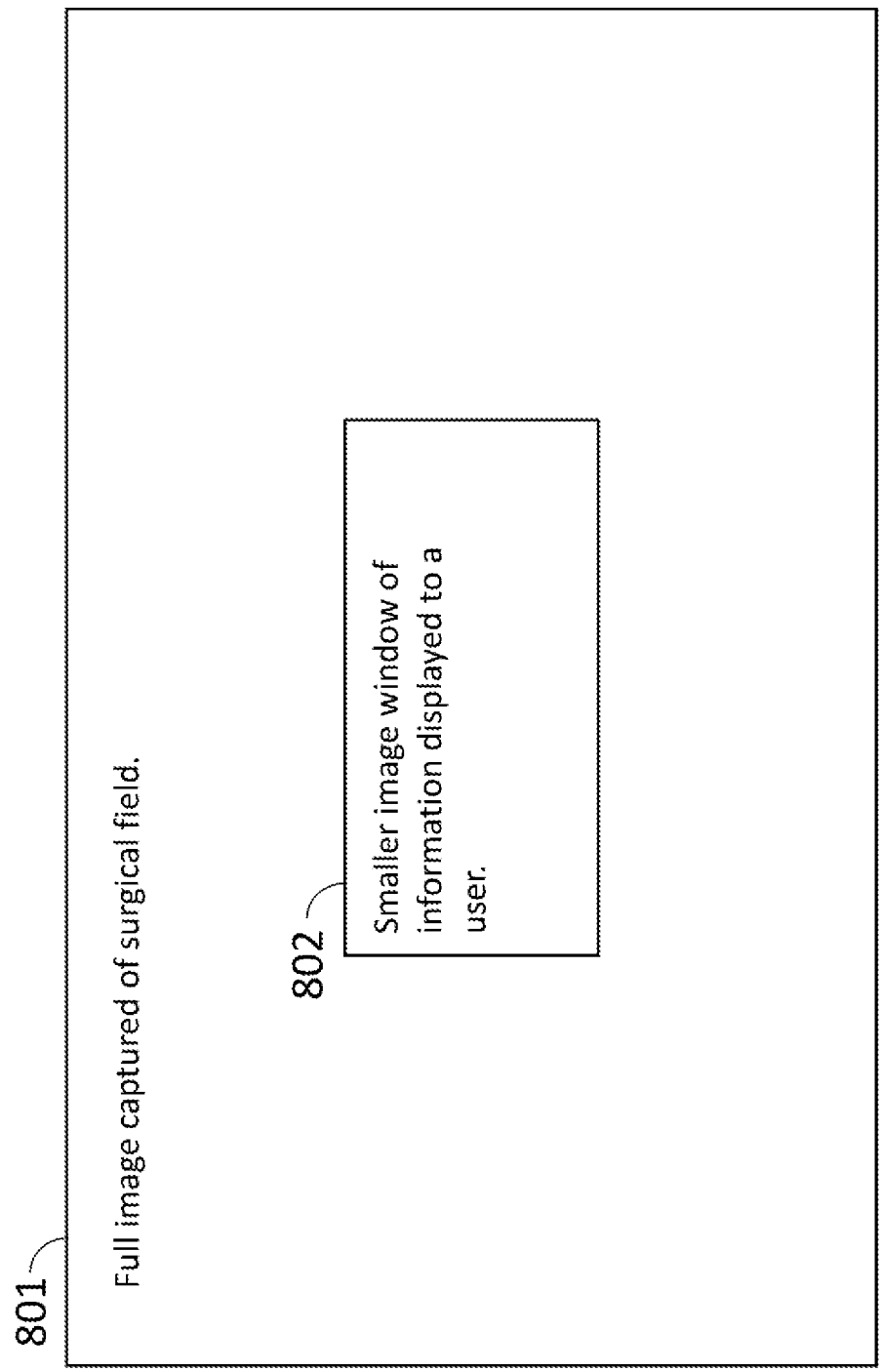
FIG. 10 depicts a high level relationship between a field of view and a window within that field of view.

In a situation where data is captured regarding field of view which is larger than the field of view required for a procedure, a method such as shown in FIG. 9 may be used to allow a user to control the field of view which would be displayed (e.g., via display (29)). In the method of FIG. 9, a first field of view would be captured in step (901). This may be done, for example, by an imaging device (17) capturing data regarding all portions of a surgical field which could then be collected by its sensor(s). Next, in step (902) a second field of view would be displayed. This may be done, for example, by extracting a portion of the data from the first field of view (e.g., a 72×42 degree window from a 270 degree field of view), and rendering an image from that portion of the data (e.g., on display (29)). On a first iteration of a method such as shown in FIG. 9, this may be done using a default portion of the first field of view. For example, a center portion of the first field of view may be extracted as shown in FIG. 10. Subsequently, as described below, the relationship of the second field of view to the first field of view may be changed, such as by moving, resizing, or reshaping the second field of view.

Figure 11:
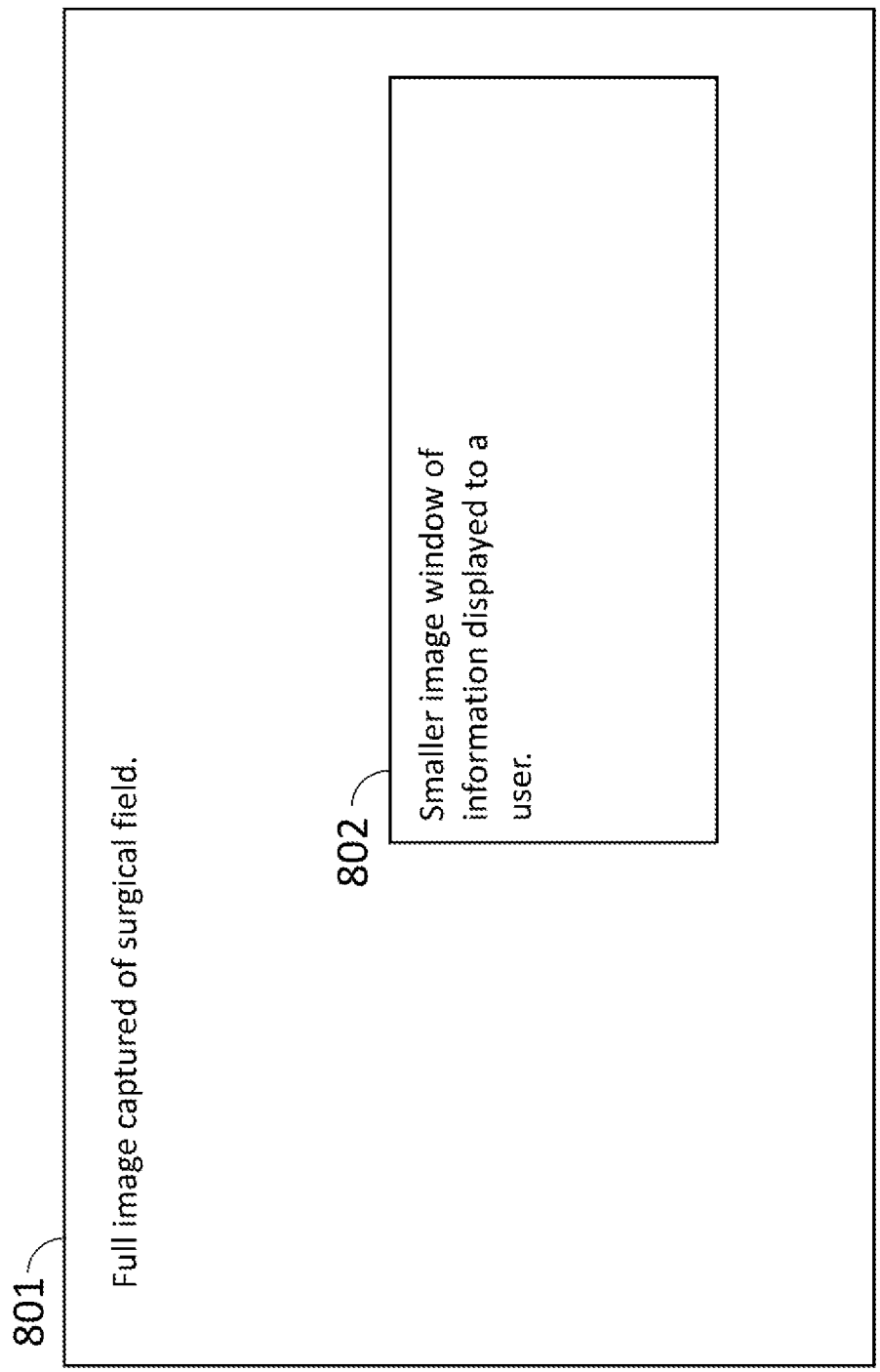
FIG. 11 depicts a high level relationship between a field of view and a window within that field of view.

During a procedure, a surgeon may input a command to change the view being presented to him or her (e.g., using controls (30) presented by an interface of an imaging system (27)). In the method of FIG. 9, when this view change is received in step (903), a determination (904) would be made as to whether the change required device movement. For example, if the surgeon provided a command indicating that the second field of view should be resized, rotated, or translated, a determination could be made whether the bounds of the second field of view following the resizing, translation or rotation would still be in the first field of view. If the change would result in the second field of view extending beyond the bounds of the first field of view, then, in step (905) the imaging device used to capture the first field of view could be moved to ensure that the first field of view included all necessary data. For example, it may be disconnected and reinserted into a new trocar that would provide visibility of all necessary data (port hopping), or may be reoriented without being repositioned, such as by a scrub nurse or a robotic effector. Alternatively, if the change did not result in the second field of view extending beyond the bounds of the first field of view (e.g., the second field of view was translated, rotated or resized within the first field of view), then, in step (906) the second field of view may be updated without requiring movement of the imaging device. An illustration of this is provided in FIG. 11, which shows how a second field of view (802) may be translated and resized while remaining within the bounds of the first field of view (801).

Variations on windowing applications may also be implemented. For example, in some cases, a second field of view displayed to a surgeon may be augmented with information captured in the first field of view. For instance, if one or more critical structures was located inside the first field of view but outside the second field of view, a system implemented based on this disclosure may detect the critical structure in the data captured for the first field of view. In such a case, the display of the second field of view presented to the surgeon may be enhanced with information indicating the location of the critical structure. This information may include data such as the distance of the field of view relative to the critical structure, and/or other information such as the distance of the critical structure to the working devices being used in a procedure. In some cases, a divergence between the total data captured for a first field of view and the data needed to be displayed for a smaller second field of view may be utilized in order to reduce the computational load associated with providing real time imaging of an anatomical field. To illustrate, consider a case in which an image of an anatomical field is captured using a multi-sensor imaging device such as show in FIG. 12.

Figure 12:
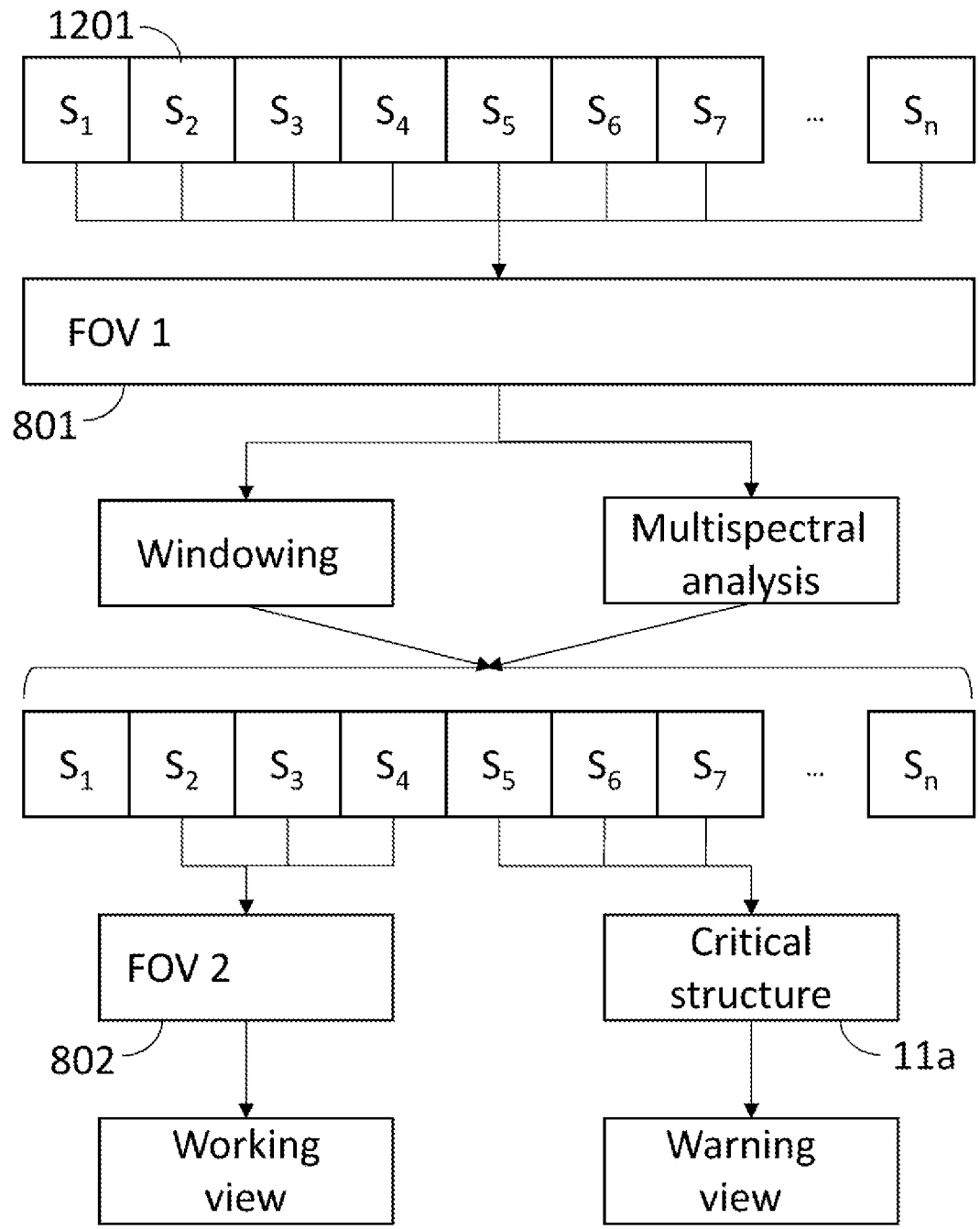
FIG. 12 a relationship between an array of sensors and portions of a field of view.

In the case such as shown in FIG. 12, an image of an anatomical field may be captured using an array of sensors (1202), comprising individual sensors $S_1, S_2, S_3, \ldots S_n$. This image captured by the full array (1202) may be the first field of view (801), and various portions of that first field of view (801) that are relevant to the procedure being performed may be identified. For example, the second field of view (802) corresponding to the portion of the anatomical field to be displayed to the surgeon may be identified based on factors such as commands provided by the surgeon, as described previously in the context of FIG. 9. Similarly, a critical structure (11a) may be identified using multispectral analysis and image recognition. The sensors from the full array which corresponded to the identified second field of view (802) and critical structure (11a) may then be identified (e.g., based on each of the sensors capturing data from a particular part of the anatomical field), and only the data from those sensors may be presented to the surgeon, such as through display of a working view (i.e., the portion of the first field of view selected for display) and/or through display of a warning view (e.g., annotations on the working view indicating relative position of the critical structure). Similarly, in addition to only displaying data from certain sensors, in some cases only the data from those sensors may be subjected to processing after being collected, such as having image recognition applied to identify a critical structure. In this type of approach, a surgical visualization system may flash an entire scene, but then track and only display or apply advanced processing to relevant data.

Additional variations may also be possible. For example, while FIG. 8 illustrated a single imaging device (17), and FIG. 12 illustrated a contiguous array of sensors (1201), in some cases multiple independently deployed imaging devices or sensors may be used to capture data regarding an anatomical field, such as is described in U.S. patent application Ser. No. 17/528,369, entitled "Surgical Visualization Image Enhancement," filed on even date herewith, published as U.S. Pat. No. 2023/0156174 on May 18, 2023, and incorporated by reference herein in its entirety. Similarly, in some cases, when an imaging device was moved (e.g., in step (905) of FIG. 9), the imaging device may simply be moved to recenter the second field of view within the (new) first field of view. However, in other cases the imaging device may be moved in a manner that seeks to reduce the likelihood of additional movement by taking into account surrounding context. For example, in some cases when an imaging device was moved, it could be moved to a position which would maximize the amount of data captured regarding portions of the anatomical field that were not include in the previous first field of view, under the theory that the need for movement meant the previously imaged portions of the field were less likely to be relevant going forward. Other variations and potential implementations are also possible, will be immediately apparent to, and could be implemented without undue experimentation by, one of ordinary skill in the art in light of this disclosure. Accordingly, the particular examples and illustrations provided herein should be understood as being illustrative only, and should not be treated as being limiting on the scope of protection provided by this document of any other document claiming the benefit of this disclosure.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical visualization system comprising: (a) a set of one or more imaging devices, wherein the set of one or more imaging devices is adapted to capture a view of an interior of a cavity of a patient; (b) a display; and (c) a processor in operative communication with the set of one or more imaging devices and the display, wherein the processor is configured to present an interface on the display, the interface comprising a second field of view of the interior of the cavity of the patient, wherein the second field of view is comprised by the first field of view.

Example 2

The surgical visualization system of Example 1, wherein: (a) the first field of view has a horizontal extent of 270 degrees; and (b) the second field of view has a horizontal extent of 72 degrees.

Example 3

The surgical visualization system of any of Examples 1-2, wherein the processor is configured to, in response to receiving a command to modify the second field of view: (a) determine a modified set of bounds, wherein the modified set of bounds are bounds for the second field of view after modifying the second field of view based on the command; (b) determine whether the modified set of bounds is comprised within the first field of view; (c) based on a determination that the modified set of bounds is not comprised by the first field of view, generate a signal to modify the first field of view to completely comprise the modified set of bounds by moving one or more imaging devices from the set of one or more imaging devices; and (d) update the interface on the display by performing acts comprising causing the display to present the second field of view with the modified set of bounds.

Example 4

The surgical visualization system of Example 3, wherein the signal to modify the first field of view is an instruction to a robotic effector to reorient the one or more imaging devices from the set of one or more imaging devices.

Example 5

The surgical visualization system of Example 3, wherein the signal to modify the first field of view is an instruction presented on the display to move an imaging device from a first port in the cavity of the patient to a second port in the cavity of the patient.

Example 6

The surgical visualization system of any of Examples 1-5, wherein the processor is configured to: (a) identify a critical structure within the first field of view; and (b) based on identifying the critical structure at a critical structure location within the first field of view and outside of the second field of view, present an indication of the critical structure location on the interface.

Example 7

The surgical visualization system of Example 6, wherein the processor is configured to: (a) identify the critical structure using spectral processing; (b) apply the spectral processing selectively to only: (i) the second field of view; and (ii) a portion of the first field of view corresponding to the critical structure.

Example 8

The surgical visualization system of Example 7, wherein: (a) the set of one or more imaging devices comprises a plurality of sensors, each of the plurality of sensors detecting data from a portion of the first field of view; (b) the processor is configured to: (i) for each sensor from the plurality of sensors, determine if that sensor is associated with the second field of view or the portion of the first field of view corresponding to the critical structure based on comparing the field of view of that sensor with the second field of view and the critical structure location; and (ii) selectively apply the spectral processing based on applying spectral processing only to data from: (A) sensors associated with the second field of view; and (B) sensors associated with the portion of the first field of view corresponding to the critical structure

Example 9

The surgical visualization system of any of Examples 1-8, wherein the set of one or more imaging devices consists of a single camera inserted through trocar to view the interior of the cavity of the patient.

Example 10

The surgical visualization system of any of Examples 1-8, wherein the set of one or more imaging devices comprises a plurality of cameras, each of which is inserted through a corresponding trocar to view the interior of the cavity of the patient.

Example 11

A method comprising: (a) capturing an image of a first field of view of an interior of a cavity of a patient using a set of one or more imaging devices; (b) a processor in operative communication with the set of one or more imaging devices presenting an image on a display, the image comprising a second field of view of the interior of the cavity of the patient, wherein the second field of view is comprised by the first field of view.

Example 12

The method of Example 11, wherein: (a) the first field of view has a horizontal extent of 270 degrees; and (b) the second field of view has a horizontal extent of 72 degrees.

Example 13

The method of any of Examples 11-12, wherein the method comprises: (a) receiving a command to modify the second field of view; (b) in response to receiving the command to modify the second field of view: (i) determining a modified set of bounds, wherein the modified set of bounds are bounds for the second field of view after modifying the second field of view based on the command; (ii) determining whether the modified set of bounds is comprised within the first field of view; (iii) based on a determination that the modified set of bounds is not comprised by the first field of view, generating a signal to modify the first field of view to completely comprise the modified set of bounds by moving one or more imaging devices from the set of one or more imaging devices; and (iv) updating the interface on the display by performing acts comprising causing the display to present the second field of view with the modified set of bounds.

Example 14

The method of Example 13, wherein the signal to modify the first field of view is an instruction to a robotic effector to reorient the one or more imaging devices from the set of one or more imaging devices.

Example 15

The method of Example 13, wherein the signal to modify the first field of view is an instruction presented on the display to move an imaging device from a first port in the cavity of the patient to a second port in the cavity of the patient.

Example 16

The method of any of Examples 11-15, wherein the method comprises: (a) identifying a critical structure within the first field of view; and (b) based on identifying the critical structure at a critical structure location within the first field of view and outside of the second field of view, presenting an indication of the critical structure location on the interface.

Example 17

The method of Example 16, wherein the processor is configured to: (a) identify the critical structure using spectral processing; (b) apply the spectral processing selectively to only: (i) the second field of view; and (ii) a portion of the first field of view corresponding to the critical structure.

Example 18

The method of Example 17, wherein: (a) the set of one or more imaging devices comprises a plurality of sensors, each of the plurality of sensors detecting data from a portion of the first field of view; (b) the processor is configured to: (i) for each sensor from the plurality of sensors, determine if that sensor is associated with the second field of view or the portion of the first field of view corresponding to the critical structure based on comparing the field of view of that sensor with the second field of view and the critical structure location; and (ii) selectively apply the spectral processing based on applying spectral processing only to data from: (A) sensors associated with the second field of view; and (B) sensors associated with the portion of the first field of view corresponding to the critical structure.

Example 19

The method of any of Examples 11-18, wherein the set of one or more imaging devices consists of a single camera inserted through trocar to view the interior of the cavity of the patient.

Example 20

The method of any of Examples 11-18, wherein the set of one or more imaging devices comprises a plurality of cameras, each of which is inserted through a corresponding trocar to view the interior of the cavity of the patient.

Example 21

A non-transitory computer readable medium having stored thereon instructions operable to configure a surgical visualization system to perform a method, the method comprising: (a) capturing an image of a first field of view of an interior of a cavity of a patient using a set of one or more imaging devices; and (b) a processor in operative communication with the set of one or more imaging devices presenting an image on a display, the image comprising a second field of view of the interior of the cavity of the patient, wherein the second field of view is comprised by the first field of view.

Example 22

The non-transitory computer readable medium of Example 21, wherein: (a) the first field of view has a horizontal extent of 270 degrees; and (b) the second field of view has a horizontal extent of 72 degrees.

Example 23

The non-transitory computer readable medium of any of Examples 21-22, wherein the method comprises, in response to receiving a command to modify the second field of view: (a) determining a modified set of bounds, wherein the modified set of bounds are bounds for the second field of view after modifying the second field of view based on the command; (b) determining whether the modified set of bounds is comprised within the first field of view; (c) based on a determination that the modified set of bounds is not comprised by the first field of view, generating a signal to modify the first field of view to completely comprise the modified set of bounds by moving one or more imaging devices from the set of one or more imaging devices; and (d) updating the interface on the display by performing acts comprising causing the display to present the second field of view with the modified set of bounds.

Example 24

The non-transitory computer readable medium of Example 23, wherein the signal to modify the first field of view is an instruction to a robotic effector to reorient the one or more imaging devices from the set of one or more imaging devices.

Example 25

The non-transitory computer readable medium of Example 23, wherein the signal to modify the first field of view is an instruction presented on the display to move an imaging device from a first port in the cavity of the patient to a second port in the cavity of the patient.

Example 26

The non-transitory computer readable medium of any of Examples 21-25, wherein the method comprises: (a) identifying a critical structure within the first field of view; and (b) based on identifying the critical structure at a critical structure location within the first field of view and outside of the second field of view, presenting an indication of the critical structure location on the interface.

Example 27

The non-transitory computer readable medium of Example 26, wherein the method comprises: (a) identifying the critical structure using spectral processing; (b) applying the spectral processing selectively to only: (i) the second field of view; and (ii) a portion of the first field of view corresponding to the critical structure.

Example 28

The non-transitory computer readable medium of Example 27, wherein: (a) the set of one or more imaging devices comprises a plurality of sensors, each of the plurality of sensors detecting data from a portion of the first field of view; (b) the method comprises: (i) for each sensor from the plurality of sensors, determining if that sensor is associated with the second field of view or the portion of the first field of view corresponding to the critical structure based on comparing the field of view of that sensor with the second field of view and the critical structure location; and (ii) selectively applying the spectral processing based on applying spectral processing only to data from: (A) sensors associated with the second field of view; and (B) sensors associated with the portion of the first field of view corresponding to the critical structure.

Example 29

The non-transitory computer readable medium of any of Examples 21-28, wherein the set of one or more imaging devices consists of a single camera inserted through trocar to view the interior of the cavity of the patient.

Example 30

The non-transitory computer readable medium of any of Examples 21-28, wherein the set of one or more imaging devices comprises a plurality of cameras, each of which is inserted through a corresponding trocar to view the interior of the cavity of the patient.

IV. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they may be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that may penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical visualization system comprising:
   (a) a set of one or more imaging devices, wherein the set of one or more imaging devices is adapted to capture a first field of view of an interior of a cavity of a patient;
   (b) a display; and
   (c) a processor in operative communication with the set of one or more imaging devices and the display, wherein the processor is configured to present an interface on the display, the interface comprising a second field of view of the interior of the cavity of the patient, wherein the second field of view is comprised by the first field of view;
   wherein the processor is configured to, in response to receiving a command to modify the second field of view:
   (i) determine a modified set of bounds, wherein the modified set of bounds are bounds for the second field of view after modifying the second field of view based on the command;
   (ii) determine whether the modified set of bounds is comprised within the first field of view;
   (iii) based on a determination that the modified set of bounds is not comprised by the first field of view, generate a signal to modify the first field of view to completely comprise the modified set of bounds by moving one or more imaging devices from the set of one or more imaging devices; and
   (iv) update the interface on the display by performing acts comprising causing the display to present the second field of view with the modified set of bounds.

2. The surgical visualization system of claim 1, wherein:
   (a) the first field of view has a horizontal extent of 270 degrees; and
   (b) the second field of view has a horizontal extent of 72 degrees.

3. The surgical visualization system of claim 1, wherein the signal to modify the first field of view is an instruction to a robotic effector to reorient the one or more imaging devices from the set of one or more imaging devices.

4. The surgical visualization system of claim 1, wherein the signal to modify the first field of view is an instruction presented on the display to move an imaging device from a first port in the cavity of the patient to a second port in the cavity of the patient.

5. The surgical visualization system of claim 1, wherein the processor is configured to:
   (a) identify a critical structure within the first field of view; and
   (b) based on identifying the critical structure at a critical structure location within the first field of view and outside of the second field of view, present an indication of the critical structure location on the interface.

6. The surgical visualization system of claim 5, wherein the processor is configured to:
   (a) identify the critical structure using spectral processing;
   (b) apply the spectral processing selectively to only:
      (i) the second field of view; and
      (ii) a portion of the first field of view corresponding to the critical structure.

7. The surgical visualization system of claim 6, wherein:
   (a) the set of one or more imaging devices comprises a plurality of sensors, each of the plurality of sensors detecting data from a portion of the first field of view;
   (b) the processor is configured to:
      (i) for each sensor from the plurality of sensors, determine if that sensor is associated with the second field of view or the portion of the first field of view corresponding to the critical structure based on comparing the field of view of that sensor with the second field of view and the critical structure location; and
      (ii) selectively apply the spectral processing based on applying spectral processing only to data from:
         (A) sensors from the plurality of sensors associated with the second field of view; and
         (B) sensors from the plurality of sensors associated with the portion of the first field of view corresponding to the critical structure.

8. The surgical visualization system of claim 1, wherein the set of one or more imaging devices consists of a single camera inserted through a trocar to view the interior of the cavity of the patient.

9. The surgical visualization system of claim 1, wherein the set of one or more imaging devices comprises a plurality of cameras, each of which is inserted through a corresponding trocar to view the interior of the cavity of the patient.

10. A method comprising:
   (a) capturing an image of a first field of view of an interior of a cavity of a patient using a set of one or more imaging devices, wherein the set of one or more imaging devices comprises a plurality of sensors, each of the plurality of sensors detecting data from a portion of the first field of view;
   (b) presenting an interface on a display, the interface comprising a second field of view of the interior of the cavity of the patient, wherein the second field of view is comprised by the first field of view;
   (c) for each sensor from the plurality of sensors, determining that that sensor is associated with the second field of view or a portion of the first field of view corresponding to a critical structure when the portion of the first field of view from which that sensor detects data overlaps with, respectively, the second field of view or the portion of the first field of view corresponding to the critical structure; and (d) selectively applying spectral processing only to data from:
  (i) sensors from the plurality of sensors associated with the second field of view; and
  (ii) sensors from the plurality of sensors associated with the portion of the first field of view corresponding to the critical structure.

11. The method of claim 10, wherein the method comprises:
  (a) receiving a command to modify the second field of view;
  (b) in response to receiving the command to modify the second field of view:
    (i) determining a modified set of bounds, wherein the modified set of bounds are bounds for the second field of view after modifying the second field of view based on the command;
    (ii) determining whether the modified set of bounds is comprised within the first field of view;
    (iii) based on a determination that the modified set of bounds is not comprised by the first field of view, generating a signal to modify the first field of view to completely comprise the modified set of bounds by moving one or more imaging devices from the set of one or more imaging devices; and
    (iv) updating the interface on the display by performing acts comprising causing the display to present the second field of view with the modified set of bounds.

12. The method of claim 10, wherein the method comprises:
  (a) identifying the critical structure within the first field of view; and
  (b) based on identifying the critical structure at a critical structure location within the first field of view and outside of the second field of view, presenting an indication of the critical structure location on the interface.

13. The method of claim 12, wherein the method comprises
identifying the critical structure using spectral processing.

14. A non-transitory computer readable medium having stored thereon instructions operable to configure a surgical visualization system to perform a method, the method comprising:
  (a) capturing an image of a first field of view of an interior of a cavity of a patient using a set of one or more imaging devices, wherein the set of one or more imaging devices comprises a plurality of sensors, each of the plurality of sensors being configured to detect data from a portion of the first field of view corresponding to that sensor;
  (b) presenting an interface on a display, the interface comprising a second field of view of the interior of the cavity of the patient, wherein the second field of view is comprised by the first field of view; and
  (c) selectively applying spectral processing only to data from sensors from the plurality of sensors which are configured to detect data from the second field of view and/or a portion of the first field of view corresponding to a critical structure.

15. The non-transitory computer readable medium of claim 14, wherein the method comprises, in response to receiving a command to modify the second field of view:
  (a) determining a modified set of bounds, wherein the modified set of bounds are bounds for the second field of view after modifying the second field of view based on the command;
  (b) determining whether the modified set of bounds is comprised within the first field of view;
  (c) based on a determination that the modified set of bounds is not comprised by the first field of view, generating a signal to modify the first field of view to completely comprise the modified set of bounds by moving one or more imaging devices from the set of one or more imaging devices; and
  (d) updating the interface on the display by performing acts comprising causing the display to present the second field of view with the modified set of bounds.

16. The non-transitory computer readable medium of claim 14, wherein the method comprises:
  (a) identifying the critical structure within the first field of view; and
  (b) based on identifying the critical structure at a critical structure location within the first field of view and outside of the second field of view, presenting an indication of the critical structure location on the interface.

17. The non-transitory computer readable medium of claim 16, wherein the method comprises
identifying the critical structure using spectral processing.

* * * * *